(12) United States Patent  
Aikawa et al.

(10) Patent No.: US 8,449,115 B2
(45) Date of Patent: May 28, 2013

(54) OPHTHALMOLOGIC APPARATUS (75) Inventors: Satoshi Aikawa, Yokohama (JP);
Hideyuki Ooban, Kawaguchi (JP);
Tomoyuki Iwanaga, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/620,479

(22) Filed: Nov. 17, 2009

(65) Prior Publication Data

US 2010/0123872 A1    May 20, 2010

(30) Foreign Application Priority Data

Nov. 19, 2008    (JP) .................................. 2008-295805

(51) Int. Cl.
*A61B 3/14* (2006.01)
*A61B 3/10* (2006.01)

(52) U.S. Cl.
USPC ............ 351/208; 351/205; 351/211; 351/221

(58) Field of Classification Search
USPC .......... 351/208, 205–206, 200, 221, 210–211
See application file for complete search history.

(56) References Cited

U.S. PATENT DOCUMENTS

| 2005/0134798 | A1* | 6/2005 | Hirohara et al. | 351/221 |
| 2007/0147817 | A1* | 6/2007 | Li et al. | 396/133 |
| 2008/0015553 | A1* | 1/2008 | Zacharias | 606/4 |
| 2010/0182567 | A1* | 7/2010 | Nouchi et al. | 351/208 |

FOREIGN PATENT DOCUMENTS

| JP | 60-207636 A | 10/1985 |
| JP | S60-207636 A | 10/1985 |
| JP | 9066030 A | 3/1997 |
| JP | 2005-087301 A | 4/2005 |

* cited by examiner

*Primary Examiner* — Dawayne A Pinkney
(74) *Attorney, Agent, or Firm* — Canon U.S.A., Inc., IP Division (57) ABSTRACT

An opthalmologic apparatus changes the wavelength of index light, which is projected on an eye to be examined, by selecting the light emission of a visible LED and an infrared LED, and changes the position of a split unit along an optical axis based on the selection.

28 Claims, 7 Drawing Sheets

FIG. 1

FIG. 2A
LIGHT PATH DURING LIGHT EMISSION OF VISIBLE LED

FIG. 2B
SPLIT IMAGE DURING LIGHT EMISSION OF VISIBLE LED

FIG. 2C
LIGHT PATH DURING LIGHT EMISSION OF NEAR-INFRARED LED

FIG. 2D
SPLIT IMAGE DURING LIGHT EMISSION OF NEAR-INFRARED LED

FIG. 7

OPHTHALMOLOGIC APPARATUS

BACKGROUND OF THE INVENTION

1. Field of the Invention

The present invention relates to an opthalmologic apparatus, and more specifically, to a technique for focusing in an opthalmologic apparatus.

2. Description of the Related Art

A technique about a fundus camera, which selects and uses a plurality of illumination light sources, is discussed in Japanese Patent Application Laid-Open No. 09-066030. In this case, if an illumination light source is changed, it is necessary to improve visibility by changing the wavelength of index light. However, a difference in the length of the light path is generated due to the difference in the wavelength of the index light, so that it is difficult to confirm an accurate focal point. In the technique discussed in Japanese Patent Application Laid-Open No. 09-066030, the difference in the length of light path is absorbed by changing a relay lens of an illumination system according to the illumination light source.

However, since a relay lens barrel of the illumination system is large, it is difficult to replace the relay lens barrel while maintaining the accuracy of the optical system.

SUMMARY OF THE INVENTION

The present invention is directed to an opthalmologic apparatus that can perform focusing easily even though the wavelength of an illumination light source is changed.

According to an aspect of the present invention, an opthalmologic apparatus includes: a first optical unit configured to illuminate an eye to be examined; a second optical unit configured to form an image of one of portions of the eye to be examined illuminated by the first optical unit; an index projecting unit configured to project index light on the eye to be examined; a changing unit configured to change the wavelength of the index light projected by the index projecting unit; and a position control unit configured to control the position of the index projecting unit on an optical axis according to the wavelength of the index light changed by the changing unit. The index light represents the state of a focal point in the opthalmologic apparatus.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

An opthalmologic apparatus according to a first exemplary embodiment of the present invention will be described with reference to FIGS. 1 to 3.

Figure 1:
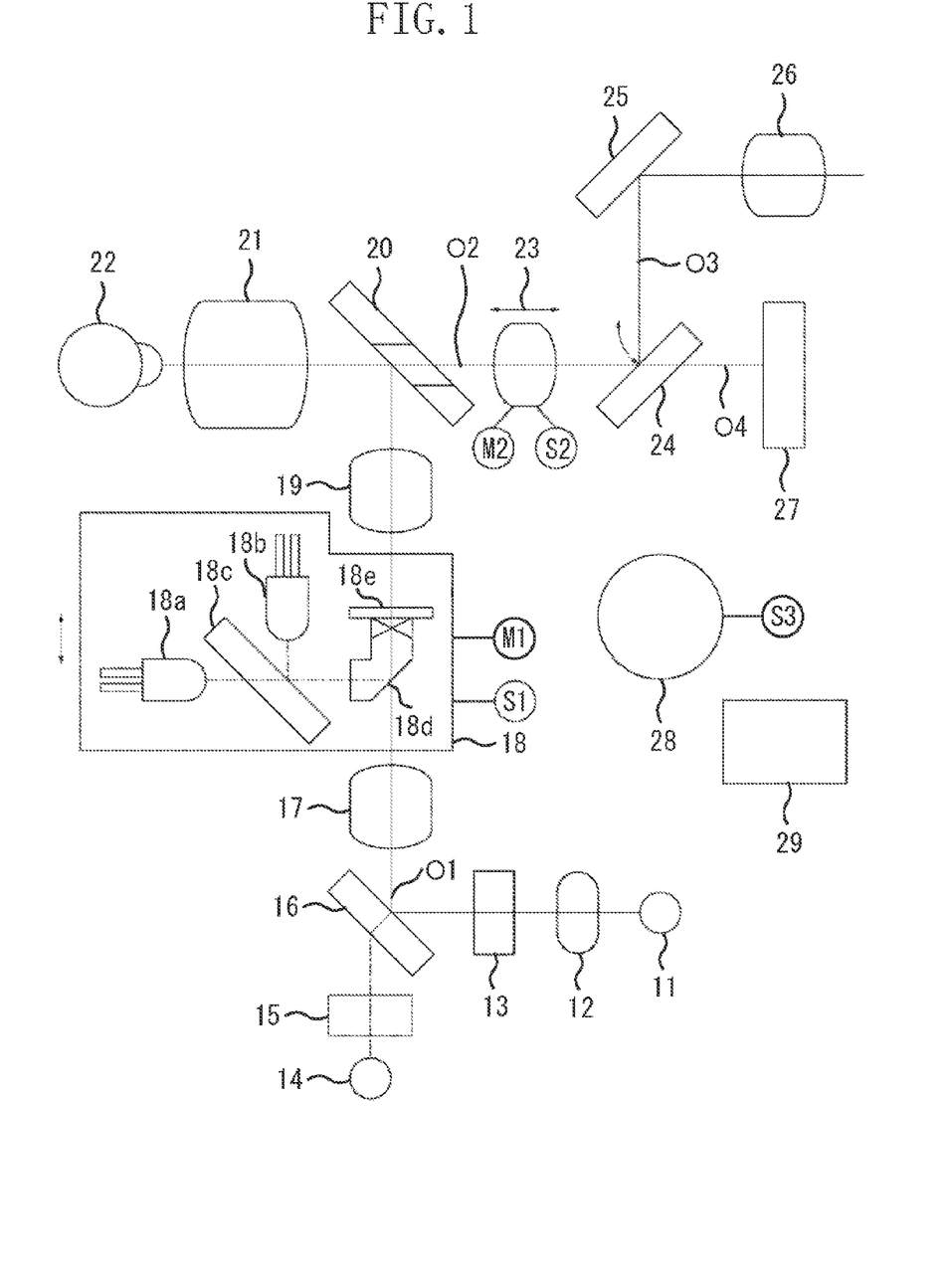
FIG. 1 illustrates a configuration of an opthalmologic apparatus according to a first exemplary embodiment.

FIG. 1 is a schematic view illustrating a configuration of an opthalmologic apparatus.

A halogen lamp 11 is a light source having a visible wavelength, and is used to visually observe the eye fundus of a subject. A xenon lamp 12 is a light source having a visible wavelength, and is used to visually photograph the eye fundus of a subject. A visual ring slit 13 is a mask that makes the illumination light emitted from the halogen lamp 11 and the xenon lamp 12 have a ring shape.

An infrared light-emitting diode (LED) 14 is a light source that is used for infrared observation. An infrared ring slit 15 is a mask that makes the illumination light emitted from the infrared LED 14 have a ring shape.

An illuminating mirror 16 is a dichroic mirror, and has characteristics to reflect visible light and transmit infrared light. Light paths of ring-shaped visual illumination and ring-shaped infrared illumination are combined by the illuminating mirror 16.

An optical axis of a first optical system O1 is indicated by a solid line or a dashed-dotted line. The first optical system O1 illuminates an eye 22 to be examined with the light, which is emitted from the light sources. Ring-shaped illumination light forms an image on the eye to be examined by an illuminating relay lens 17 and an illuminating relay lens 19.

A split unit 18 as an index projecting unit projects index light, which shows the state of a focal point, on the eye 22 to be examined. A split unit 18 includes light sources 18a and 18b having different wavelengths having different wavelengths. A dichroic mirror 18c transmits light emitted from the light source 18a and reflects light emitted from the light source 18b.

The light, which is emitted from one of the light sources 18a and 18b, is divided by a split prism 18d, and two straight-line split images are formed by a split mask 18e. The straight-line split images are projected on the eye 22 to be examined as index light. If the focal point of the opthalmologic apparatus and the position of the eye 22 to be examined match each other, the projected index light forms one linear image. If the focal point of the opthalmologic apparatus and the position of the eye to be examined do not match each other, the projected index light forms two linear images.

In the present exemplary embodiment, the index light is projected on the eye fundus. However, the invention is not limited thereto, and the index light may be projected on an anterior eye portion. The light sources 18a and 18b have wavelengths where good visibility can be obtained in the visual observation and infrared observation respectively. For example, an LED is used as alight source, and the light sources 18a and 18b will be referred to hereinafter as a visible LED 18a and an infrared LED 18b, respectively.

Further, the split unit 18 is inserted in the first optical system O1 and is moved along the optical axis in a direction indicated by an arrow in FIG. 1 at the time of the observation. The split unit 18 includes a mechanism (not illustrated) for moving the position of the split unit 18 to move the position thereof that emits the index light along the direction of the optical axis. The mechanism (not illustrated) includes a split drive motor M1.

Furthermore, the opthalmologic apparatus includes a mechanism (not illustrated) for retracting the split unit from the first optical system O1 during the photographing. A split position detection circuit S1 detects the position of the split unit 18. A perforated mirror 20 is a total reflection mirror with a hole at the center thereof, the ring-shaped illumination light is reflected by an outer circumferential mirror portion, and an image of the fundus of the eye to be examined passes through the central hole.

An objective lens 21 illuminates the eye 22 to be examined with the ring-shaped illumination light that has passed through the perforated mirror 20. Light reflected from the eye 22 to be examined passes through the objective lens and forms an image at the center of the perforated mirror 20.

A second optical system O2 is an optical system that forms an image with the light reflected from the eye 22 to be examined. Further, the second optical system O2 is optically branched into an observing optical system O3 and a photographing optical system O4. The observing optical system O3 includes a finder eyepiece lens 26, and the photographing optical system O4 includes a sensor 27 including an imaging element.

An optical axis, which reaches the finder eyepiece lens 26 and the imaging element 27 from the image of the fundus of the eye to be examined, is illustrated by a solid line. The second optical system O2 forms an image of one of the portions of the eye 22 to be examined, such as an anterior eye portion and an eye fundus portion.

A focus lens 23 is a lens for adjusting a focal point (which may be hereinafter referred to as a "focus") of the photographing light flux that passes through the central hole of the perforated mirror 20, and adjusts the focal point by moving along a direction indicated by an arrow in FIG. 1.

A focus lens drive motor M2 is used to move the focus lens 23, and a focus lens position detection circuit S2 detects the position of the focus lens 23.

A movable mirror 24 is positioned as illustrated in FIG. 1 at the time of visual observation, and guides photographing light to the observing optical system O3. Further, the movable mirror retracts by rotating as illustrated by an arrow in FIG. 1 at the time of infrared observation and photographing, and guides the photographing light to the photographing optical system O4.

A stationary mirror 25 reflects the photographing light toward a finder, and enables an examiner to observe the eye to be examined through the finder eyepiece lens 26.

The sensor 27 including an imaging element performs photoelectric conversion of the photographing light. Then, a digital processing circuit (not illustrated) converts the photographing light into digital data. The digital data is displayed on a display (not illustrated) at the time of the infrared observation, and is recorded on a recording medium (not illustrated) at the time of the photographing.

An examiner can adjust a focus state by operating a focus adjustment knob 28, and the focus position is detected by a focus adjustment position detection circuit S3.

An examiner selects an observation light source from visible light and infrared light by operating a light source selection switch 29 as a selection unit. Accordingly, the eye 22 to be examined is illuminated with the light selected between the near-infrared light and the visible light.

The split unit 18 as an index projecting unit will be described in detail with reference to FIGS. 1, and 2A to 2D.

Figure 2A:
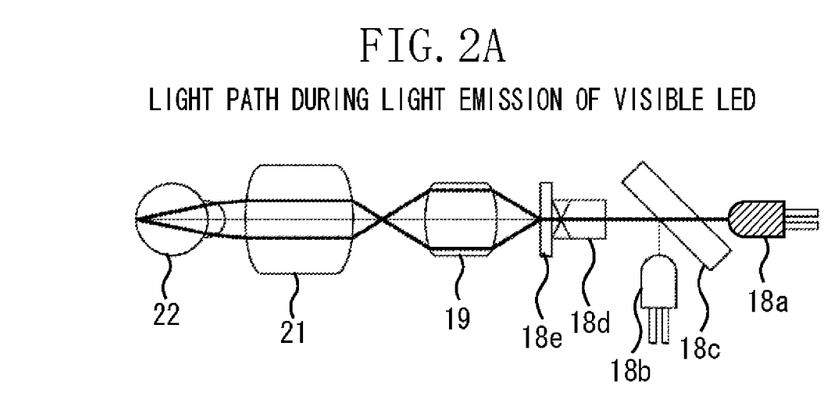
FIGS. 2A, 2B, 2C, and 2D illustrate a split optical system according to the first exemplary embodiment.
Figure 2B:
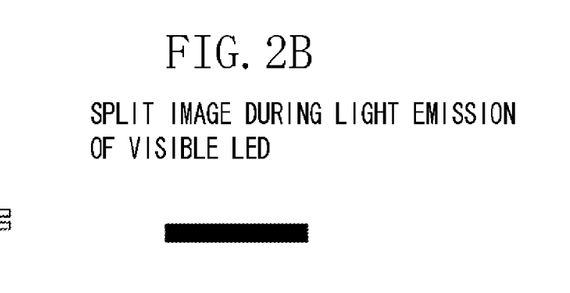
Figure 2C:
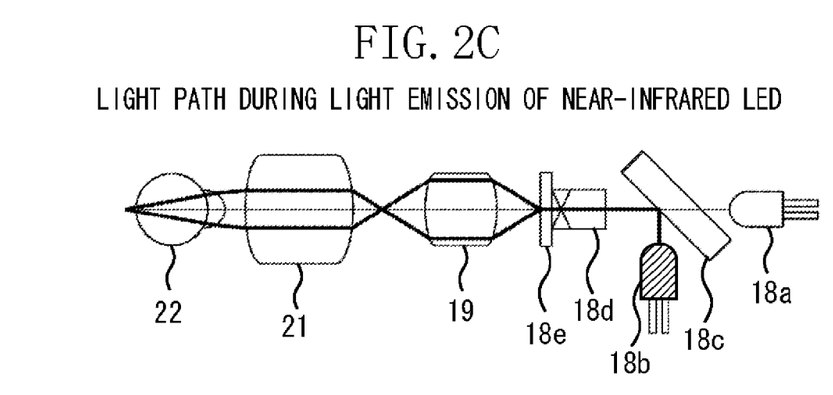

FIGS. 2A and 2C illustrate a split optical system according to the first exemplary embodiment of the invention. The reflection surface of the split prism 18d and the reflection surface of the perforated mirror 20 are omitted, and only the optical system is illustrated.

When the visible LED 18a is turned on, the light flux thereof passes through the dichroic mirror 18c and is divided by the split prism 18d. The divided two split images become linear images by the split mask 18e disposed at a position close to the split prism 18d. Two split images are formed on the perforated mirror 20 by the illuminating relay lens 19.

In addition, an image reflected by the perforated mirror 20 is projected on the fundus of the eye 22 to be examined by the objective lens 21. When the focal point of the second optical system is positioned on the fundus of the eye 22 to be examined, the divided two split images are projected in the shape of a line as illustrated in FIG. 2B.

If the LED that is turned on is changed to the near-infrared LED 18b, the length of light path is changed due to the chromatic aberration caused by the difference in color of the LEDs. If the near-infrared LED 18b is turned on, the light flux thereof is reflected by the dichroic mirror 18c and then travels along the same light path as the visible LED 18a.

Figure 2D:
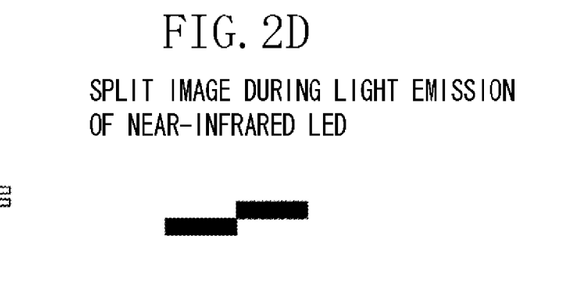

However, the length of light path is increased due to the chromatic aberration, so that an image is formed at a position more distant than the fundus of the eye 22 to be examined. Further, two split images, which are projected on the fundus of the eye 22 to be examined, have a difference in level between the left side line (image) and right side line (image) as illustrated in FIG. 2D. More specifically, if the opthalmologic apparatus is not in an in-focus state, the split images are separated into two lines in the vertical direction of the line at the left side and right side as illustrated in FIG. 2D.

Figure 3:
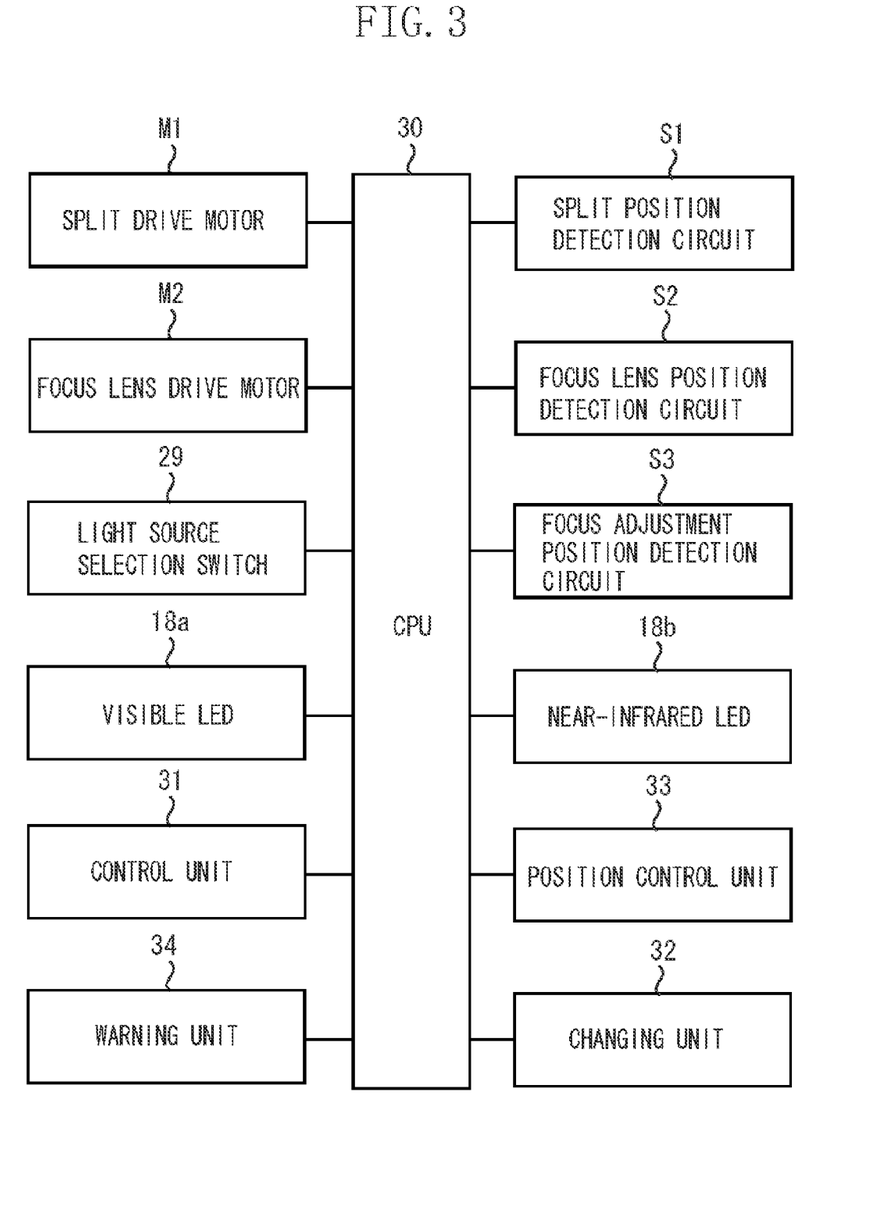
FIG. 3 is a block diagram illustrating an opthalmologic apparatus according to the first exemplary embodiment.

FIG. 3 is a block diagram illustrating an opthalmologic apparatus according to the first exemplary embodiment.

A central processing unit (CPU) 30 mainly controls the operation of each of components that includes a control unit 31, a changing unit 32, a position control unit 33, and a warning unit 34. A memory 101 (not illustrated) stores a control program that is executed by the CPU 30, or provides a work area when the CPU 30 executes a program.

The control unit 31 and the warning unit 34 control the photographing operation of the sensor 27. The changing unit 32 changes the wavelength of the index light by controlling the lighting of the visible LED 18a and the near-infrared LED 18b.

Further, the position control unit 33 controls the movement of the focus lens 23 and the movement of the split unit 18 by controlling the split drive motor M1, the split position detection circuit S1, the focus lens drive motor M2, and the focus lens position detection circuit S2 via the CPU 30.

Furthermore, signals, which are output from the focus adjustment position detection circuit S3 and the light source selection switch 29, are connected to the control unit 31, the changing unit 32, the position control unit 33, and the warning unit 34 via the CPU 30. Accordingly, the control of the light source, the movement of the focus lens 23, and the movement of the split unit 18 are performed.

Figure 4:
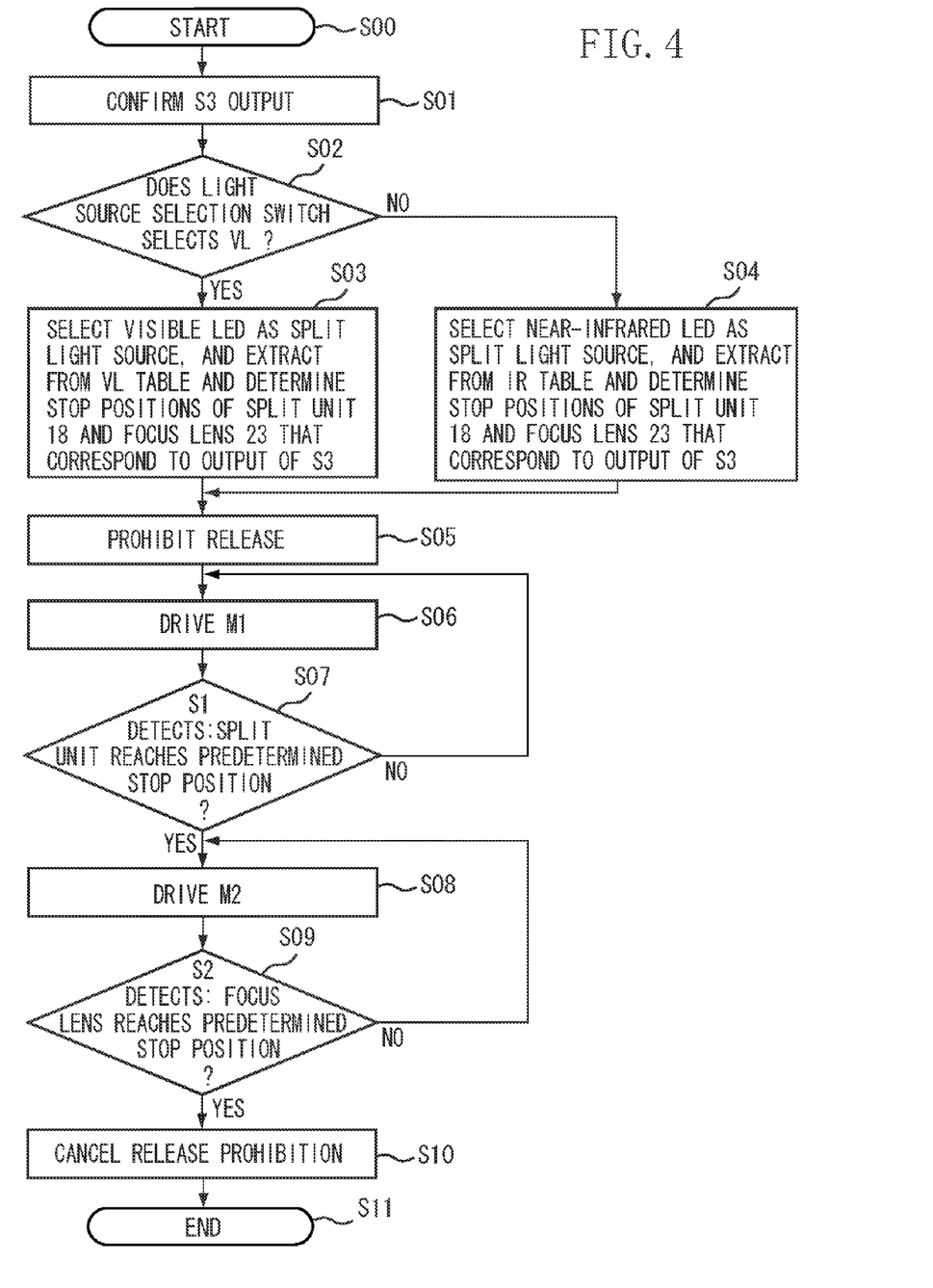
FIG. 4 is a flowchart illustrating a focusing operation according to the first exemplary embodiment.

FIG. 4 is a flowchart illustrating a focusing operation according to the first exemplary embodiment of the invention.

In step S00, the flow of the focusing operation starts under the control of the CPU 30.

In step S01, the focus adjustment position detection circuit S3 detects the stop position of the focus adjustment knob 28 and outputs the stop position to the CPU 30. Accordingly, the CPU 30 recognizes the focal position (focus position) that is set by an examiner.

In step S02, the CPU 30 confirms the state of the light source selection switch 29. If visible light observation represented by "VL" is selected (YES in step S02), the process proceeds to step S03. If the infrared observation represented by "IR" is selected (YES in step S02), the process proceeds to step S04.

In step S03, the changing unit 32 selects the visible LED 18a as a split light source, and uses the wavelength of the index light for the visual observation. The CPU 30 reads a VL table that is stored in the memory 101. The VL table stores the stop positions of the split unit 18 and the focus lens 23 that correspond to the outputs of the focus adjustment position detection circuit S3. Then, the process proceeds to step S05.

In step S04, the changing unit 32 selects the infrared LED 18b as the split light source, and uses the wavelength of the index light for the infrared observation. Further, the CPU 30 reads an IR table that is stored in the memory 101. The IR table stores the stop positions of the split unit 18 and the focus lens 23 that correspond to the outputs of the focus adjustment position detection circuit S3. Then, the process proceeds to step S05.

That is, in steps S03 and S04, the changing unit 32 changes the wavelength of the index light by making one of the visible LED 18a and the infrared LED 18b emit light according to the light source selected by the light source selection switch 29.

In step S05, while the split unit 18 and the focus lens 23 move, the split unit and the focus lens are not in focus. Further, the control unit 31 prohibits a photographing operation of the sensor 37 to prevent an out-of-focus photograph. In the present exemplary embodiment, the control unit has prohibited the photographing operation of the sensor. However, the control unit may "give warning" for the photographing operation in consideration of release priority. In this case, the warning unit 32 gives warning for the photographing operation of the sensor 27.

In step S06, the position control unit 33 drives the split drive motor M1 based on the information of the read table. Further, the split drive motor moves the split unit 18 to a position, which is obtained from the table based on the output signal of the split position detection circuit S1, under the control of the position control unit 33.

The position control unit 33 confirms whether the split unit 18 reaches a predetermined stop position. If the split unit 18 does not reach the predetermined stop position (NO in step S07), the process returns to step S06. If the split unit reaches the predetermined stop position (YES in step S07), the process proceeds to step S08.

In step S08, the position control unit 33 drives the focus lens drive motor M2 based on the information read from the table. Further, the focus lens drive motor moves the focus lens 23 to a position, which is obtained from the table based on the output signal of the focus lens position detection circuit S2, under the control of the position control unit 33.

In step S09, the position control unit 33 detects the output of the focus lens position detection circuit S2, and confirms the stop position of the focus lens 23. If the focus lens does not reach a predetermined stop position (NO in step S09), the process proceeds to step S08. If the focus lens reaches the predetermined stop position (YES in step S09), the process proceeds to step S10.

In step S10, the control unit 31 cancels the release prohibition operation that has been prohibited before. Then, the process proceeds to step S11. Then, the entire focusing operation is completed.

Figure 5:
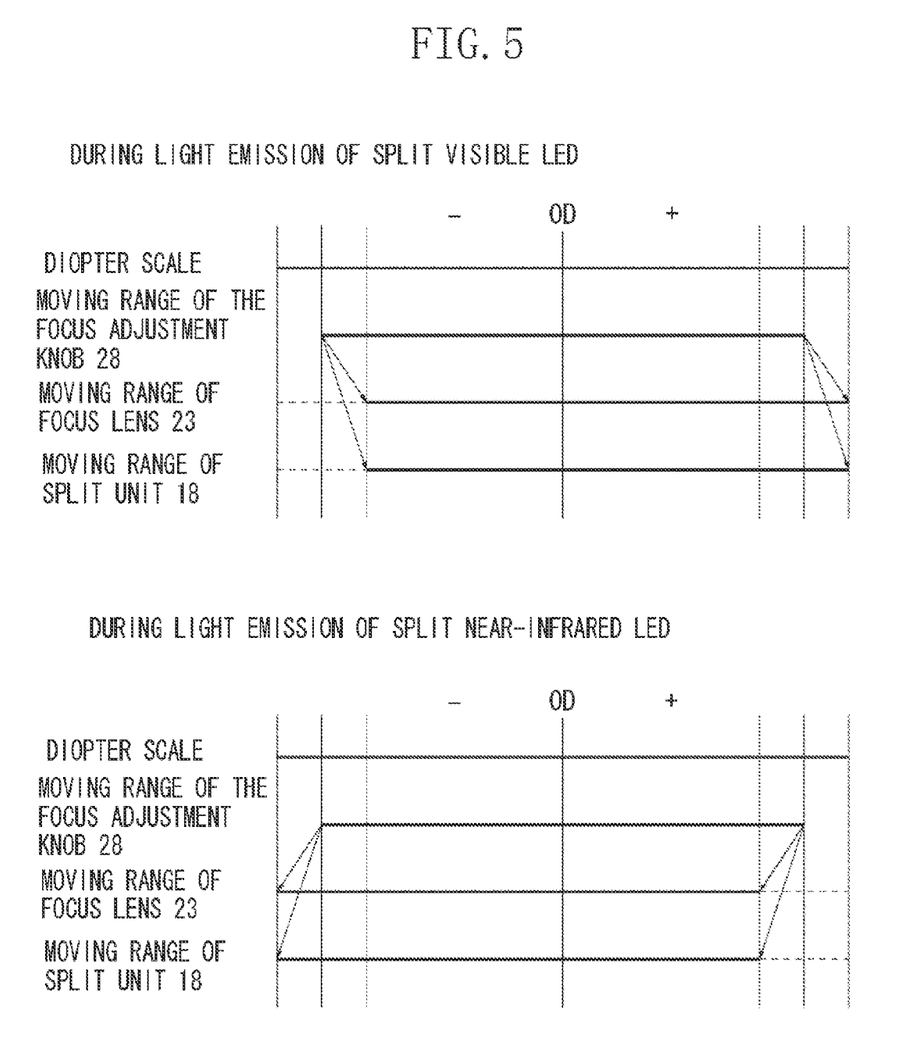
FIG. 5 illustrates a focusing operation according to the first exemplary embodiment.

FIG. 5 illustrates the focusing operation according to the first exemplary embodiment of the invention. As described above referring to FIG. 2, 0D of the focus lens 23 is shifted by the selection of a light source having different wavelength.

In the present exemplary embodiment, the drive motors move the focus lens 23 and the split unit 18 based on the position of the focus adjustment knob 28 as a reference. For this reason, it is necessary to shift the position of the focus lens 23 and the split unit 18 with respect to 0D as illustrated in FIG. 5.

Further, it also is necessary to control the moving ranges of the focus lens 23 and the split unit 18. In the ranges indicated by a dotted line, the focus lens 23 and the split unit 18 can operate, but the operation thereof is restricted by the CPU 30.

The invention is not limited to the above flow of the process, and the light emission timing of the visible LED 18a and the infrared LED 18b and the movement timing of the split unit 18 may be or may not be simultaneous. The light emission timing of the visible LED 18a and the infrared LED 18b and the movement timing of the focus lens 23 may be or may not be simultaneous.

With the above configuration, the split unit 18 and the focus lens 23 can be independently controlled according to the selection of the light source having different wavelength and the operation of the focus adjustment knob 28.

As described above, it may be possible to correct the change of the length of light path, which occurs when the wavelength of the index light is changed, by moving the split unit 18. Accordingly, the configuration of the opthalmologic apparatus may be simplified, so that the reliability may be improved and the size thereof may be reduced. As a result, the opthalmologic apparatus may become user-friendly.

Further, even when the index light is changed to the index light having excellent visibility to the illumination light when the illumination light is changed, it may be possible to correct the change of the length of light path by the simple configuration.

Furthermore, the photographing operation of the sensor 27 is restricted, so that an image is not recorded when the state of the image is not stable. Accordingly, it may be possible to prevent the failure in photographing.

A second exemplary embodiment of the invention will be described with reference to FIG. 6.

Figure 6:
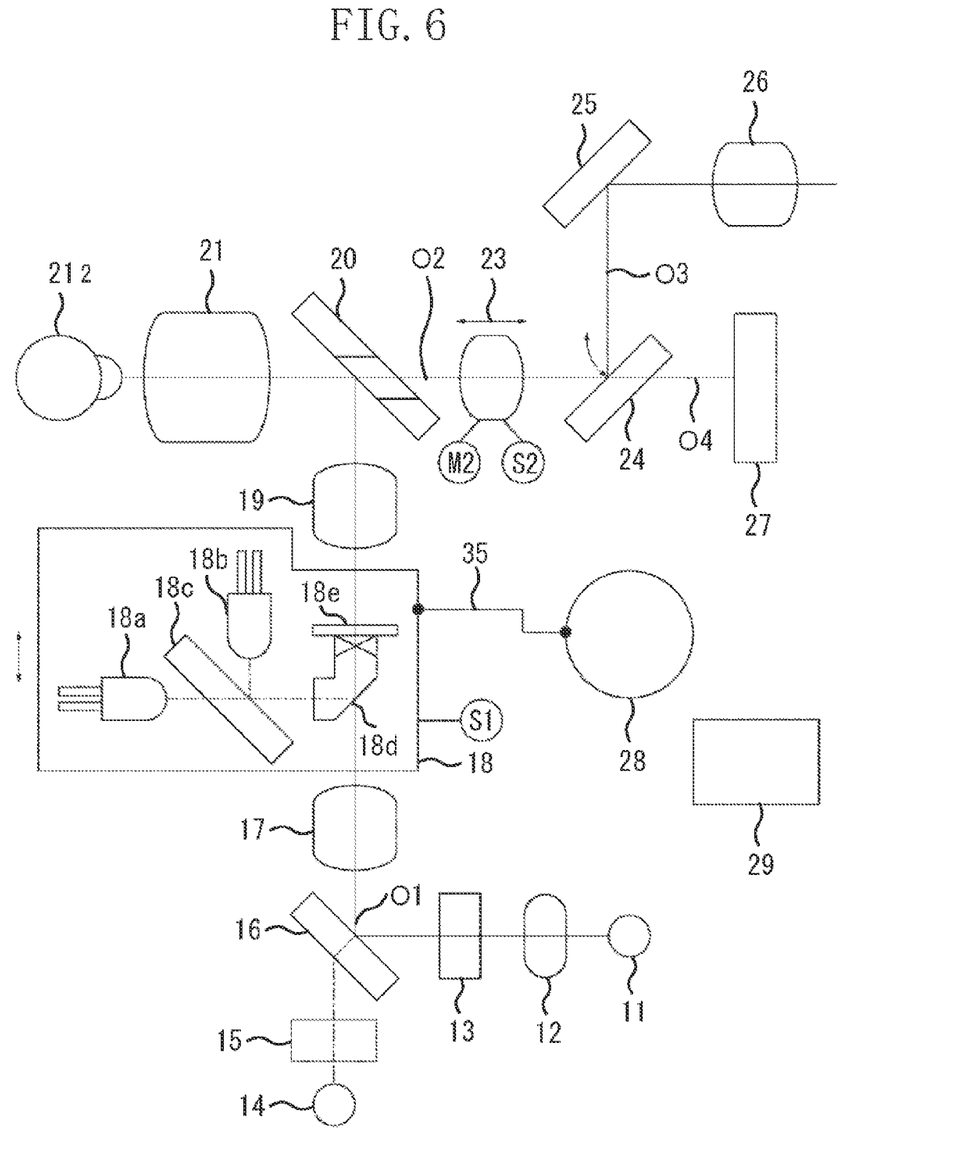
FIG. 6 is illustrates a configuration of an opthalmologic apparatus according to a second exemplary embodiment.

FIG. 6 illustrates a configuration of an opthalmologic apparatus according to a second exemplary embodiment of the invention.

Components identical to those of FIG. 1 are denoted by the same reference numerals, and the description thereof will not be repeated.

A component to be newly added is an interlocking member 35, which is a mechanical structure. The interlocking member 35 makes the focus adjustment knob 28 and the split unit 18 interlocked with each other by a known mechanical structure, such as a gear or a lever.

Accordingly, the motor M1 that drives the split unit 18 and the focus adjustment position detection circuit S3 that detects the stop position of the focus adjustment knob 28 are not needed. In this case, the focus adjustment knob 28 and the member, which interlocks with the focus adjustment knob 28 by a mechanical structure, correspond to a position control unit.

With the above configuration, if an examiner operates the focus adjustment knob 28 to perform a focus changing operation, the split unit 18 moves while interlocking with the focus adjustment knob and it may be possible to control the stop position of the focus lens 23 based on the stop position of the split unit 18 according to the state of the light source selection switch 29.

A third exemplary embodiment of the present invention will be described with reference to FIG. 7.

Figure 7:
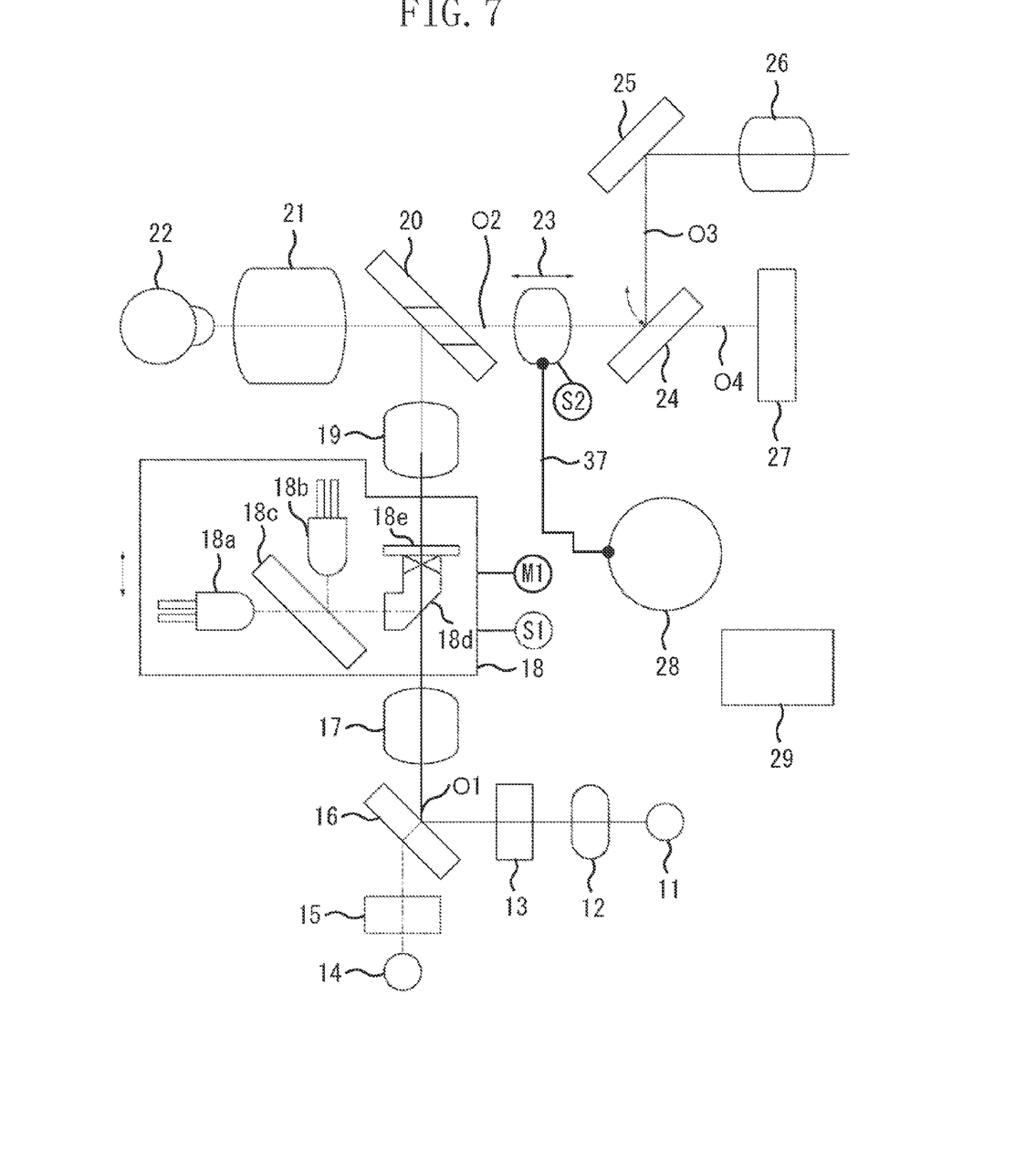
FIG. 7 is illustrates a configuration of an opthalmologic apparatus according to a third exemplary embodiment.

FIG. 7 illustrates the configuration of a third exemplary embodiment of the present invention.

Components common to those in FIG. 1 are denoted by the same reference numerals, and the description thereof will not be repeated.

A component to be newly added is an interlocking member 37, which is a mechanical structure, and the focus adjustment knob 28 and the focus lens 23 are directly interlocked with each other by a known mechanical structure, such as a gear or a lever.

Accordingly, the motor M2 that drives the focus lens 23 and the focus adjustment position detection circuit S3 that detects the stop position of the focus adjustment knob 28 are not needed. In this case, the focus adjustment knob 28 and the member, which is interlocked with the focus adjustment knob 28 by a mechanical structure, correspond to a position control unit.

With the above configuration, if an examiner operates the focus adjustment knob 28 to perform a focus changing operation, the focus lens 23 moves while interlocking with the focus adjustment knob 28 and it may be possible to control the stop position of the split unit 18 according to the stop position of the focus lens 23 in consideration of the state of the light source selection switch 29.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2008-295805 filed Nov. 19, 2008, which is hereby incorporated by reference herein in its entirety.

What is claimed is:

1. An ophthalmologic apparatus comprising:
   an illumination optical system configured to illuminate an eye to be examined with an illumination light;
   a selecting unit configured to select a wavelength of focusing index light projected on an eye to be examined via the illumination optical system according to a wavelength of the illumination light emitted by the illumination optical system;
   an index projecting unit configured to project the focusing index light of the selected wavelength on the eye to be examined and comprising a focusing index light source configured to emit the focusing index light of the selected wavelength; and
   a position control unit configured to move the index projecting unit to a position on an optical axis of the illumination optical system corresponding to the selected wavelength according to a result of the selection of the selecting unit.

2. The ophthalmologic apparatus according to claim 1, wherein the illumination optical system is configured to be capable of selecting a near-infrared wavelength or a visible light wavelength.

3. The ophthalmologic apparatus according to claim 1, further comprising a focus lens for focusing a fundus of the eye to be examined, and
   wherein the position control unit controls the positions of the index projecting unit and the focus lens along the optical axis while interlocking the index projecting unit and the focus lens.

4. The ophthalmologic apparatus according to claim 3, further comprising an imaging element, and a control unit that restricts a photographing operation of the imaging element when one of the focus lens and the index projecting unit moves.

5. The ophthalmologic apparatus according to claim 3, further comprising:
   a warning unit configured to give warning for the photographing operation of the sensor while at least one of the focus lens and the index projecting unit moves.

6. The ophthalmologic apparatus according to claim 1, wherein the index projecting unit projects the index light, which is used to detect a focus state between the ophthalmologic apparatus and the fundus of the eye to be examined, on the fundus of the eye to be examined.

7. The ophthalmologic apparatus according to claim 1, further comprising a first optical unit configured to illuminate the eye to be examined with the illumination light; and
   a second optical unit configured to form an image of a portion of the eye to be examined that is illuminated via the first optical unit;
   wherein the second optical unit forms an image of the fundus of the eye to be examined, which is illuminated by the first optical unit.

8. The ophthalmologic apparatus according to claim 1, further comprising a focusing unit disposed in a photographing optical system and configured to focus a fundus of the eye to be examined,
   wherein the position control unit includes an obtaining unit configured to obtain a position on the optical axis to which the focusing unit is moved after the wavelength of the illumination light is selected based on the illumination light of the wavelength to illuminate the eye to be examined and the position of the focusing unit on the optical axis.

9. The ophthalmologic apparatus according to claim 8, wherein the obtaining unit is a table to obtain the position on the optical axis to which the focusing unit is moved after the wavelength of the illumination light is selected.

10. The ophthalmologic apparatus according to claim 8, wherein the position control unit controls the position of the focusing unit on the optical axis and retreats the index projecting unit out of an optical path when illumination light within a visible range is selected.

11. The ophthalmologic apparatus according to claim 1, wherein, if the wavelength of the focus index light is switched on infrared area and visible area by the selecting unit, the position control unit moves the index projecting unit based on the optical wavelength difference which occurs resulting from the switching.

12. The ophthalmologic apparatus according to claim 1, further comprising a storing unit configured to store the position of the illumination light system on the optical axis corresponding to the wavelength selected by the selecting unit;
   wherein the position control unit moves the index projecting unit to the position stored by the storing unit.

13. The ophthalmologic apparatus according to claim 12, wherein the storing unit stores the position of the illumination light system on the optical axis as a table corresponding to each of the wavelength of the focus index light; and
   wherein the position control unit moves the index projecting unit to the position corresponding to the selected wavelength obtained based on the wavelength selected by the selecting unit and the table.

14. The ophthalmologic apparatus according to claim 1, further comprising a focusing unit disposed in a photographing optical system and configured to focus a fundus of the eye to be examined;
  wherein the position control unit controls the focus unit independently from the index projecting unit, and moves the focus unit to the position of the illumination light system corresponding to the wavelength selected by the selecting unit on the optical axis.

15. An ophthalmologic apparatus comprising:
  an illumination optical system configured to illuminate an eye to be examined with an illumination light;
  an index projecting unit configured to project focusing index light on an eye to be examined and comprising a focusing index light source configured to emit focusing index light of a wavelength selected according to a wavelength of the illumination light; and
  a control unit configured to restrict a photographing operation of an imaging element if the index projecting unit moves.

16. An ophthalmologic apparatus comprising:
  an illumination optical system configured to illuminate an eye to be examined with an illumination light;
  an index projecting unit configured to project index light on the eye to be examined, which is used to detect a focal state in the ophthalmologic apparatus, the index projecting unit comprising a focusing index light source configured to emit focusing index light of a wavelength selected according to a wavelength of the illumination light; and
  a warning unit configured to give warning for a photographing operation of an imaging element if the index projecting unit moves.

17. An ophthalmologic apparatus comprising:
  an illumination optical system configured to illuminate an eye to be examined with an illumination light;
  a selecting unit configured to select a wavelength of an illumination light with which an eye to be examined is illuminated via the illumination optical system according to a wavelength of the illumination light emitted by the illumination optical system;
  an index projecting unit configured to project a focusing index light corresponding to the selected wavelength on the eye to be examined according to the result of the selection of the selecting unit, the index projecting unit comprising a focusing index light source configured to emit the focusing index light of the selected wavelength; and
  a control unit configured to move the index projecting unit to a position on an optical axis of the illumination optical system corresponding to the selected wavelength according to the result of the selection of the selection unit.

18. The ophthalmologic apparatus according to claim 17, wherein the control unit selects a visible light as the focusing index light when the illumination light is a visible light, and the control unit selects an infrared light as the focusing index light when the illumination light is an infrared light.

19. An ophthalmologic system comprising:
  an illumination optical system configured to illuminate an eye to be examined with an illumination light;
  a selecting unit configured to select a wavelength of focusing index light projected on an eye to be examined via the illumination optical system according to a wavelength of the illumination light emitted by the illumination optical system;
  an index projecting unit configured to project the focusing index light of the selected wavelength on the eye to be examined and comprising a focusing index light source configured to emit the focusing index light of the selected wavelength; and
  a position control unit configured to move the index projecting unit to a position on an optical axis of the illumination optical system corresponding to the selected wavelength according to the result of the selection of the selecting unit.

20. An ophthalmologic apparatus comprising:
  an illumination optical system configured to illuminate an eye to be examined with an illumination light, wherein a wavelength of the illumination light is changeable;
  an index projecting unit configured to project a focusing index light of a wavelength corresponding to a wavelength of the illumination light on the eye to be examined;
  a selecting unit configured to select the wavelength of the focusing index light corresponding to the wavelength of the illumination light on the eye to be examined; and
  a control unit configured to correct a length of light path of the focusing index light based on the wavelength selected by the selecting unit.

21. The ophthalmologic apparatus according to claim 20, wherein the control unit corrects a difference between a length of light path of the focusing index light before the selecting unit selects the wavelength and a length of light path of the focusing index light after the selecting unit selects the wavelength.

22. The ophthalmologic apparatus according to claim 20, wherein the control unit corrects a change of the length of light path, and
  wherein the change of the length of light path occurs when wavelength of the focusing index light is changed.

23. The ophthalmologic apparatus according to claim 22, wherein the change of the length of light path is caused by a difference between the wavelength selected by the selecting unit and a wavelength before being selected by the selecting unit.

24. The ophthalmologic apparatus according to claim 20, wherein the control unit moves the index projecting unit to a position on an optical axis of the illumination optical system corresponding to the selected wavelength.

25. The ophthalmologic apparatus according to claim 20, further comprising a focusing index light source configured to emit the focusing index light of the selected wavelength.

26. An ophthalmologic method comprising:
  illuminating an eye to be examined with an illumination light;
  projecting a focusing index light of a wavelength corresponding to a wavelength of the illumination light on the eye to be examined;
  selecting the wavelength of the focusing index light corresponding to the wavelength of the illumination light on the eye to be examined; and
  correcting a length of light path based on the wavelength of the focusing index light selected as corresponding to the wavelength of the illumination light on the eye to be examined.

27. A non-transitory computer-readable recording medium having computer-executable instructions stored thereon for performing the method according to claim 26.

28. The ophthalmologic method according to claim 26, wherein the index projecting unit is moved to a position on an optical axis of the illumination optical system corresponding to the selected wavelength.

* * * * *